United States Patent [19]

Henco et al.

[11] Patent Number: 5,637,455
[45] Date of Patent: Jun. 10, 1997

[54] HIV-2 VIRUS VARIANTS

[75] Inventors: Karsten Henco, Erkrath; Hagen von Briesen, Kronberg; Andreas Immelmann, Dusseldorf; Herbert Kühnel, Egelsbach; Ursula Dietrich, Eschborn; Helga Rübsamen-Waigmann, Bad Soden am Taunus; Michalina Adamski, Frankfurt, all of Germany

[73] Assignees: Qiagen GmbH, Hilden; Chemotherapeutisches Forschunginstitut Georg-Speyer-Haus, Frankfurt am Main, both of Germany

[21] Appl. No.: 358,575

[22] Filed: Dec. 14, 1994

Related U.S. Application Data

[63] Continuation of Ser. No. 994,081, Dec. 16, 1992, abandoned, which is a continuation of Ser. No. 365,568, Jun. 14, 1989, abandoned.

[30] Foreign Application Priority Data

Jun. 18, 1988 [DE] Germany ................... 38 20 223.9

[51] Int. Cl.⁶ .................................................. G01N 33/53
[52] U.S. Cl. ........................ 435/5; 435/7.1; 435/7.2; 435/7.21; 435/7.29; 435/7.9; 435/235.1; 435/239; 435/974; 530/810; 530/815; 530/826
[58] Field of Search ................... 435/5, 7.1, 7.2, 435/7.21, 7.29, 7.9, 974, 240.2, 235.1, 239; 422/55–57; 530/810, 815, 826

[56] References Cited

U.S. PATENT DOCUMENTS 4,956,292  9/1990  Chermann et al. .................. 435/5

FOREIGN PATENT DOCUMENTS 0327801  8/1989  European Pat. Off. .
WO8909815  10/1989  WIPO .

OTHER PUBLICATIONS

H. Rubsamen–Waigmann et al., Isolation of Variants of Lymphocytopathic Retroviruses From the Peripheral Blood and Cerebrospinal Fluid of Patients with ARC or AIDs, Journal of Medical Virology 19:335–344 (1986).

H. von Briesen et al., Isolation Frequency and Growth Properties of HIV–Variants: Multiple Simultaneous Variants in a Patient Demonstrated by Molecular Cloning, Journal of Medical Virology 23:51–66 (1987).
A.B. Rabson et al., "Molecular Organization of the AIDS Retrovirus" vol. 40, pp. 477–480 Mar. 1985.
S.K. Arya et al., "New human and simian HIV–related retroviruses process functional transactivator (tat) gene" Nature, vol. 328, Aug. 6, 1987, pp. 548–550.
H. Kuhnel et al., "Molecular cloning of two West African human immunodeficiency virus type 2 isolates that replicate well inmacrophages . . . " Proc. Natl. Acad. Sci. USA, vol. 86, Apr. 1989, pp. 2383–2387.
Mireille Guyader et al., "Genomeorganization and transactivation of the human immunodeficiency virus type 2" Nature, vol. 326, Apr. 1987, pp. 662–669.
Beatrice H. Hahn, et al., "Molecular cloning and characterization of the HTLV–III virus associates with AIDS" Nature, vol. 312, Nov. 8, 1984, pp. 166–169.
Jan Albert et al., "A New Human Retrovirus Isolate of West African Origin (SBL–6669) and Its Relationship to HTLV–IV, LAV–II, and HTLV–IIIB"; vol. 3, No. 1, 1987, Aids Research and Human Retroviruses, Mary Ann Liebert, Inc., Publishers.
Wiley et al, Proc. Natl Acad. Sci. USA, 83:7089–93 (1986).
Gartner et al, Science, 233: 215–219 (1986).
Koenig et al, Science, 233:1089–93 (1986).
Cheng–Mayer et al, Proc. Natl Acad Sci. USA, 84:3526–30 (1987).
Koyanagi et al, Science, 236:819–22 (1987).
Saunders Dictionary & Encyclopedia of Laboratory Medicine & Technology 1984 pp. 216–217.

Primary Examiner—Christine M. Nucker
Assistant Examiner—Jeffrey Stucker
Attorney, Agent, or Firm—Jacobson, Price, Holman & Stern, PLLC

[57] ABSTRACT

HIV-2 virus variants, namely virus HIV D194 and virus HIV D205, which can be cloned from the corresponding virus isolate HIV D194 (ECACC V 87122303) or from the infected cell line HUT 194 (ECACC V 87122306) or from the virus isolate HIV D205 (ECACC V 87122304), respectively, and their RNA or RNA-fragments and DNA and DNA-fragments derived therefrom and/or proteins and the use thereof for diagnostics and therapy.

14 Claims, 24 Drawing Sheets

FIG. 1

|  | Nucleotide Sequence | Amino Acid Sequence |
|---|---|---|
| gp41 | about 15% | about 21% |
| p24 | about 13% | about 8% |

```
                D    V    W    H    L    F    E    T    S    I    K    P    C
HIV2  ROD      GAT  GTC  TGG  CAT  CTA  TTC  GAG  ACA  TCA  ATA  AAA  CCA  TGT
HIV2  D194     ...  ...  ...  AGA  ...  ..T  ...  ...  ...  ...  ...  ...  ...
                D    V    W    R    L    F    E    T    S    I    K    P    C

V    K    L    T    P    L    C    V    A    M    K    C    S
HIV2  ROD      GTC  AAA  CTA  ACA  CCT  TTA  TGT  GTA  GCA  ATG  AAA  TGC  AGC
HIV2  D194     ...  ..G  T.G  ..G  ..C  C..  ...  .G   ..G  ...  ..T  ...T  --
                V    K    L    T    P    L    C    V    A    M    K    C    -

S    T    E    S    S    T    G    N    N    T    T    S    K
HIV2  ROD      xxx  xxx  xxx  xxx  xxx  xxx  xxx  xxx  xxx  xxx  xxx  xxx  xxx
HIV2  D194      --   --   --   --   --   --   --   --  ..T  .T.  ..T  ...   --
                -    -    -    -    -    -    -    -    N    I    T    S    -

S    T    S    T    T    T    T    T    P    T    D    Q    E
HIV2  ROD      AGC  ACA  AGC  ACA  ACC  ACA  ACC  ACA  CCC  ACA  GAC  CAG  GAG
HIV2  D194      --   --  G.G  ..T  ...  G.G  ...  C.G  AGT  C..  CCA  A.C  ATT
                -    -    G    T    T    A    T    P    S    P    P    N    I

Q    E    I    S    E    D    T    P    C    A    R    A    D
HIV2  ROD      CAA  GAG  ATA  AGT  GAG  GAT  ACT  CCA  TGC  GCA  CGC  GCA  GAC
HIV2  D194     AC.  ATA  ...  GA.  ..A  A..  T..  A.C  ..T  AT.  G..  .AC  .GC
                T    I    I    D    E    N    S    T    C    I    G    D    G
```

FIG. 4

```
        10          20         30          40         50          60
AGTCGCTCTG  CGGAGAGGCT GGCAGATTGA  GCCCTGGGAG GTTCTCTCCA  GCACTAGCAG
        70          80         90         100        110         120
GTAGAGCCTG  GGTGTTCCCT GCTAGACTCT  CACCAGTGCT TGGCCGGCAC  TGGGCAGACG
       130         140        150         160        170         180
GCTCCACGCT  TGCTTGCTTA AAGACCTCTT  AATAAAGCTG CCAGTTAGAA  GCAAGTTAAG
       190         200        210         220        230         240
TGTGTGTTCC  CATCTCTCCT AGTCGCCGCC  TGGTCATTCG GTGTTCATCT  GAGTAACAAG
       250         260        270         280        290         300
ACCCTGGTCT  GTTAGGACCC TTCCCGCTTT  GAGAATCCAA GGCAGGAAAA  TCCCTAGCAG
       310         320        330         340        350         360
GTTGGCGCCC  GAACAGGGAC TTGAAAGAGG  ACTGAGAAGC CCTGGAACAC  GGCTGAGTGA
       370         380        390         400        410         420
AGGCAGTAAG  GGCGGCAGGA ACAAACCACG  ACGGAGTGCT CCTAGAAAAG  CGCGGGCCGA
       430         440        450         460        470         480
GGTACCGAAG  CGGCGTGTGG AGCGGGAGTG  AAAGAGGCCT CCGGGTGAAG  GTAAGTACCT
       490         500        510         520        530         540
ACACCGAAAA  CTGTAGCCAG AAAAGGCTTG  TTATCCTACC TTTAGACAGG  TAGAAGATTG
       550         560        570         580        590         600
TGGGAGATGG  GCGCGAGAAA CTCCGTCTTG  AGAGGGAAAA AAGCAGACGA  ATTAGAAAAA
       610         620        630         640        650         660
GTTAGGTTAC  GGCCCAACGG AAAGAAAAGA  TACAGGTTAA AACATGTTGT  GTGGGCAGCG
       670         680        690         700        710         720
AATGAATTAG  ACAGATTCGG ATTGGCAGAG  AGCCTGTTGG AATCAAAAGA  AGGTTGCCAA
       730         740        750         760        770         780
AAGATTCTTA  AAGTTTTAGA ACCATTAGTA  CCAACAGGGT CAGAAAATTT  AAAAAGCCTT
       790         800        810         820        830         840
TTTAATACCG  TCTGCGTCAT TTGGTGCTTG  CACGCAGAAG AGAAAGTGAA  AGATACTGAA
       850         860        870         880        890         900
GAAGCAAAGA  AACTAGCACA GAGACATCTA  GTGGCAGAAA CAGGAACTGC  AGAGAAAATG
       910         920        930         940        950         960
CCAAATATAA  GTAGACCAAC AGCACCACCT  AGTGGGAAAG GGAGGAAACT  TCCCCGTGCA
       970         980        990        1000       1010        1020
ACAGGCAGGC  GGCAACTATA TCCATGTGCC  GCTGAGCCCC CGAACTCTAA  ATGCTTGGGT
      1030        1040       1050        1060       1070        1080
AAAATTAGTA  GAGGAAAAGA AGTTCGGGGC  AGAAGTAGTG CCAGGATTTC  AGGCACTCTC
      1090        1100       1110        1120       1130        1140
AGAAGGCTGC  ACGCCCTATG ATATCAATCA  AATGCTTAAT TGTGTGGGCG  ATCACCAAGC
```

FIG. 4A

```
     1150       1160       1170       1180       1190       1200
AGCTATGCAA ATAATCAGAG AAATTATTAA TGAGGAAGCA GCAGATTGGG ATGCGCAGCA
     1210       1220       1230       1240       1250       1260
CCCAATACCA GGCCCCTTAC CAGCAGGGCA GCTTAGAGAC CCAAGGGGGT CTGACATAGC
     1270       1280       1290       1300       1310       1320
AGGAACAACA AGCACAGTAG ATGAACAGAT CCAGTGGATG TATAGGCAAC CAAATCCCGT
     1330       1340       1350       1360       1370       1380
GCCGGTAGGG AACATCTACA GGAGATGGAT CCAGATAGGG CTACAGAAAT GTGTCAGGAT
     1390       1400       1410       1420       1430       1440
GTACAACCCA ACTAACATCT TAGATGTGAA GCAGGGACCA AAAGAATCGT TCCAGAGCTA
     1450       1460       1470       1480       1490       1500
TGTAGACAGA TTCTACAAAA GCCTAAGGGC AGAACAAACA GACCCGGCTG TAAAAAATTG
     1510       1520       1530       1540       1550       1560
GATGACCCAA ACGCTGCTAA TACAGAATGC CAACCCAGAC TGCAAGTTAG TATTAAAAGG
     1570       1580       1590       1600       1610       1620
ACTAGGGATG AATCCCACCC TAGAGGAGAT GCTGACTGCC TGCCAGGGAG TAGGCGGACC
     1630       1640       1650       1660       1670       1680
AAGCCAGAAA GCCAGACTAA TGGCTGAAGC CCTAAAGGAG GCTTTGACGC CAGCCCTAT
     1690       1700       1710       1720       1730       1740
CCCATTTGCA GCAGCCCAAC AAAGAAGGGC AATTAGGTGT TGGAATTGTG GAAAGGAGGG
     1750       1760       1770       1780       1790       1800
ACACTCGGCG AAACAGTGCC GAGCACCCAG AAGACAGGGC TGCTGGAAGT GTGGCAAGTC
     1810       1820       1830       1840       1850       1860
AGGACACATC ATGGCAAACT GCCCGGAAAG ACAGGCAGGT TTTTTAGGGA TGGGCCCACG
     1870       1880       1890       1900       1910       1920
GGGAAAGCAG CCCCGCAACT TCCCCGCGGC CCAAGCTCCT CAGGGGCTGA TACCAACAGC
     1930       1940       1950       1960       1970       1980
ACCCCCAATA GATCCAGCAG TGGACCTGTT GGAGAAATAT ATGCAGCAAG GGAGAAAGCA
     1990       2000       2010       2020       2030       2040
GAGAGAGCAG AGGGAGAGAC CATACAAGGA GGTGACGGAG GACTTACTGC ACCTCGAGCA
     2050       2060       2070       2080       2090       2100
GGGAGAGACG CCCCACAGAG GGGCGACAGA GGACTTGCTA CACCTCAATT CTCTCTTTGG
     2110       2120       2130       2140       2150       2160
AAAAGACCAG TAGTCACAGC ATTCATCGAG GATCAGCCGG TAGAAGTCTT ACTAGACACA
     2170       2180       2190       2200       2210       2220
GGAGCTGATG ACTCAATAGT AGCAGGAATA GAGTTAGGGG ACAATTACAC TCCAAAAATA
     2230       2240       2250       2260       2270       2280
GTGGGGGGAA TAGGGGGATT CATAAATACC AAAGAATATA AAATGTAGA AATAAAGGTA
     2290       2300       2310       2320       2330       2340
CTAAATAAAA GAGTAAGAGC CACCATAATG ACAGGAGATA CCCCAATCAA CATTTTTGGC
```

FIG. 4B

```
     2350       2360       2370       2380       2390       2400
AGAAATATTC TGGCAACCTT AGGCATGTCA TTAAACCTAC CAGTCGCCAA GTTAGACCCA
     2410       2420       2430       2440       2450       2460
ATAAAAGTAA CATTGAAGCC AGGGAAAGAT GGACCAAGGC TGAAACAATG GCCCCTAACA
     2470       2480       2490       2500       2510       2520
AAAGAAAAAA TAGAAGCACT AAAAGAAATT TGTGAAAAAA TGGAAAGGGA GGGCCAACTA
     2530       2540       2550       2560       2570       2580
GAAGAAGCAC CTCCAACTAA TCCTTATAAT ACCCCCACAT TTGCAATTAA GAAAAAGGAC
     2590       2600       2610       2620       2630       2640
AAGAACAAAT GGAGAATGCT AATAGATTTT AGAGAACTAA ACAGGGTGAC TCAAGATTTC
     2650       2660       2670       2680       2690       2700
ACAGAAATTC AGCTAGGAAT TCCACACCCG GCAGGATTAG CCAAAAAGAA AAGGATTACT
     2710       2720       2730       2740       2750       2760
GTACTAGATG TAGGGGATGC CTACTTTTCC ATACCACTAC ATGAAGATTT TAGGCAATAT
     2770       2780       2790       2800       2810       2820
ACTGCATTTA CCCTACCATC AGTAAACAAT GCAGAGCCAG AAAAAAGATA TGTATATAAG
     2830       2840       2850       2860       2870       2880
GTCTTACCAC AAGGATGGAA AGGATCACCA GCAATCTTTC AATTCATGAT GAGGCAAATC
     2890       2900       2910       2920       2930       2940
TTAGAACCTT TCAGAAAAGC AAACCCAGAC GTCATTCTCA TCCAATACAT GGATGATATC
     2950       2960       2970       2980       2990       3000
TTAATAGCTA GTGACAGGAC GGGTTTAGAG CATGACAAAG TAGTCCTGCA ACTAAAAGAA
     3010       3020       3030       3040       3050       3060
CTTCTGAATG GCCTAGGGTT CTCTACCCCA GATGAGAAGT TCCAAAAGGA CCCTCCGTTT
     3070       3080       3090       3100       3110       3120
CAATGGATGG GCTATGAATT GTGGCCAACT AAATGGAAAC TGCAGAAAAT ACAATTACCT
     3130       3140       3150       3160       3170       3180
CAGAAAGAAA TATGGACAGT CAATGACATC CAAAAACTAG TAGGAGTTTT GAACTGGGCG
     3190       3200       3210       3220       3230       3240
GCGCAGATCT ATCCAGGGAT AAAAACCAAG CATTTATGTA AATTGATTAG AGGAAAAATG
     3250       3260       3270       3280       3290       3300
ACACTCACAG AGGAAGTACA GTGGACAGAG TTAGCAGAGG CAGAACTAGA AGAAAACAAA
     3310       3320       3330       3340       3350       3360
ATTATCTTAA GTCAGGAACA AGAGGGATCC TACTATCAGG AAGAAGAAGA ACTAGAAGCA
     3370       3380       3390       3400       3410       3420
ACAGTCATCA AAAGCCAAGA CAATCAGTGG GCATACAAAA TACACCAGGG AGAGAGGGTT
     3430       3440       3450       3460       3470       3480
CTAAAAGTAG GAAAGTATGC GAAGATAAAA AATACTCATA CCAATGGGGT CAGACTACTA
     3490       3500       3510       3520       3530       3540
GCACAAGTAG TCCAAAAAAT AGGAAAGGAA GCACTGGTCA TTTGGGGACG AGTGCCAAAA
```

FIG. 4C

```
     3550       3560       3570       3580       3590       3600
TTTCACCTAC CGGTAGAGAG AGACACCTGG GAGCAATGGT GGGATAACTA CTGGCAAGTA
     3610       3620       3630       3640       3650       3660
ACATGGGTCC CAGAGTGGGA CTTCGTATCT ACCCCACCAC TGGTCAGGTT GACATTTAAC
     3670       3680       3690       3700       3710       3720
TTGGTAGGAG ATCCTATACC AGGCACAGAG ACCTTTTACA CAGATGGATC ATGCAATAGA
     3730       3740       3750       3760       3770       3780
CAGTCAAAAG AAGGAAAAGC AGGATATGTA ACAGATAGAG GGAGAGACAG GGTAAGAGTA
     3790       3800       3810       3820       3830       3840
TTAGAGCAAA CATCCAATCA GCAAGCAGAA CTAGAAGCCT TTGCGATGGC ACTGGCAGAC
     3850       3860       3870       3880       3890       3900
TCAGGTCCCA AGGTTAATAT CATAGTAGAC TCACAGTATG TAATGGGGAT AGTAGCAGGC
     3910       3920       3930       3940       3950       3960
CAACCAACAG AGTCAGAAAA TAGAATAGTA AACCAAATCA TTGAGGACAT GATAAAGAAA
     3970       3980       3990       4000       4010       4020
GAAGCAGTCT ATGTTGCATG GGTCCCAGCC CATAAAGGCA TAGGAGGAAA CCAGCAAGTA
     4030       4040       4050       4060       4070       4080
GACCATTTAG TAAGTCAGGG CATCAGACAA GTATTATTCC TGGAAAAGAT AGAGCCCGT
     4090       4100       4110       4120       4130       4140
CAAGAAGAAC ACGAAAAATA TCATAGCAAT ATAAAAGAAC TAACCCATAA ATTTGGAATA
     4150       4160       4170       4180       4190       4200
CCCCAACTAG TGGCAAGACA GATAGTAAAC ACATGTGCCC AATGCCAACA GAAAGGAGAA
     4210       4220       4230       4240       4250       4260
GCCATACATG GGCAAGTAAA TGCAGAAATA GGCGTTTGGC AAATGGACTG CACACACTTA
     4270       4280       4290       4300       4310       4320
GAAGGAAAAA TCATTATAGT AGCAGTGCAT GTTGCAAGTG GATTCATAGA AGCAGAAGTC
     4330       4340       4350       4360       4370       4380
ATCCCACAGG AATCAGGAAG GCAGACAGCA CTCTTCCTAT TAAAACTGGC CAGTAGGTGG
     4390       4400       4410       4420       4430       4440
CCAATAACAC ACTTGCACAC AGACAATGGC CCCAACTTCA CTTCACAGGA AGTGAAGATG
     4450       4460       4470       4480       4490       4500
GTGGCATGGT GGATAGGTAT AGAGCAATCC TTTGGAGTAC CTTACAATCC ACAAAGCCAG
     4510       4520       4530       4540       4550       4560
GGAGTAGTAG AAGCAATGAA TCACCACCTA AAAAATCAGA TAAGTAGAAT TAGAGAACAG
     4570       4580       4590       4600       4610       4620
GCAAATACAA TAGAAACAAT AGTACTAATG GCAGTTCATT GCATGAATTT TAAAAGAAGG
     4630       4640       4650       4660       4670       4680
GGAGGAATAG GGGATATGAC CCCAGCAGAA AGACTAATTA ACATGATCAC CACAGAACAA
     4690       4700       4710       4720       4730       4740
GAAATACAAT TCCTCCAAAG AAAAAATTCA AATTTTAAAA AATTCCAGGT CTATTACAGA
```

FIG. 4D

```
      4750       4760       4770       4780       4790       4800
  GAAGGCAGAG ATCAGCTGTG GAAAGGACCT GGAGAGCTAC TGTGGAAGGG AGACGGAGCA
      4810       4820       4830       4840       4850       4860
  GTCATAGTCA AGGTAGGGGC GGACATAAAA GTAGTACCAA GAAGGAAGGC CAAGATTATC
      4870       4880       4890       4900       4910       4920
  AGGGACTATG GAGGAAGGCA AGAACTGGAT AGTAGTTCCC ACCTGGAGGG TGCCAGGGAG
      4930       4940       4950       4960       4970       4980
  GATGGAGAGG TGGCATAGCC TTGTCAAGCA CCTGAAGTAC AGAACAAAAG ACTTAGAGGA
      4990       5000       5010       5020       5030       5040
  GGTGCGCTAT GTTCCCCATC ACAAGGTAGG ATGGGCATGG TGGACTTGCA GCAGGGTAAT
      5050       5060       5070       5080       5090       5100
  ATTCCCACTA GAAGGAGAAA GTCATCTAGA GATACAGGCA TATTGGAACC TAACACCAGA
      5110       5120       5130       5140       5150       5160
  AAAAGGATGG CTCTCCTCTC ATTCAGTAAG GTTAACCTGG TATACAGAAA AGTTCTGGAC
      5170       5180       5190       5200       5210       5220
  AGATGTTACC CCAGACTGTG CAGACTCCCT AATACACAGC ACTTATTTCT CTTGCTTTAC
      5230       5240       5250       5260       5270       5080
  GGCAGGTGAA GTAAGAAGAG CCATCAGAGG GGAAAAGTTA TTGTCCTGCT GCAACTACCC
      5290       5300       5310       5320       5330       5340
  CCAAGCTCAT AAAGCACAGG TACCATCACT TCAATACCTA GCCCTAGTGG TAGTGCAACA
      5350       5360       5370       5380       5390       5400
  AAATGGCAGA CCCCAGAGAA AGGGTGCCGC CAGGAAACAG TGGAGAAGAG ACCATTGGAG
      5410       5420       5430       5440       5450       5460
  AGGCCTTCGA GTGGCTAGAC AGGACTATAG AAGCCTTAAA ACGGGAGGCA GTGAACCATC
      5470       5480       5490       5500       5510       5520
  TGCCCCGAGA GCTCATTTTC CAGGTGTGGC AAAGGTCCTG GGCATATTGG CATGATGAAC
      5530       5540       5550       5560       5570       5580
  AAGGGATGTC AACAAGTTAC ACAAAGTATA GATATTTGTG CATAATGCAG AAAGCTGTGT
      5590       5600       5610       5620       5630       5640
  ATATACATTT CAAGAAGGGG TGCACTTGCC TGGGGAGAGG ACATGGCCCG GGAGGATGGA
      5650       5660       5670       5680       5690       5700
  GACCAGGACC TCCCCCTCCT CCCCCTCCAG GTCTAGTCTA ATGACTGAAG CACCAACAGA
      5710       5720       5730       5740       5750       5760
  GTTTCCCCCA GAAGATGGGA CCCCACGGAG AGAGCTAGGG AGTACCTGGG TAATAGAAAC
      5770       5780       5790       5800       5810       5820
  TCTGAAGGAA ATCAAGGAAG AAGCCTTAAA ACATTTTGAT CCCTGCTTGC TAATTGCTCT
      5830       5840       5850       5860       5870       5880
  TGGCAACTAT ATCTATAATA GACATGGAGA CACCCTTGAA GGAGCCAGAG AGCTCATTAG
      5890       5900       5910       5920       5930       5940
  AGTCCTACAA CGAGCCCTCT TCGTGCACAT CAGAGCGGGA TGTGACCGCT CAAGAAAGGG
```

FIG. 4E

```
          5950        5960        5970        5980        5990        6000
     CCAAACAAGG  AGAAGAGCTC  CTTGCCCAGC  TGCACCGACC  CCTAGAGGCA  TGCACTAACT
          6010        6020        6030        6040        6050        6060
     CATGCTATTG  TAAGCAGTGC  AGTTACCATT  GCCAGCTGTG  TTTCTTGAAA  AAAGGGCTCG
          6070        6080        6090        6100        6110        6120
     GGATATGGTA  TGCGCGACAG  GGCAGACGAA  GAAGGACTCC  AAGAAAAACT  AAGACTCATC
          6130        6140        6150        6160        6170        6180
     CGCCTCCTGC  ATCAGATAAG  TAAGTATGGA  GCCTGGTAGG  AATCAGCTGC  TTGTTGCCAT
          6190        6200        6210        6220        6230        6240
     TTTATTAACT  AGTGCTTGCT  TAATATATTG  CAAACAATAT  GTGACTGTTT  TCTATGGCAT
          6250        6260        6270        6280        6290        6300
     ACCCGCGTGG  AGAAATGCAT  CTATTCCCCT  ATTTTGTGCA  ACCAAAAATA  GAGATACTTG
          6310        6320        6330        6340        6350        6360
     GGGGACCATC  CAGTGCTTGC  CAGACAATGA  TGATTATCAG  GAAATAACCT  TAAATGTGAC
          6370        6380        6390        6400        6410        6420
     AGAAGCTTTT  GATGCATGGG  ATAATACAGT  AACAGAACAA  GCAATAGAAG  ATGTCTGGAG
          6430        6440        6450        6460        6470        6480
     ACTGTTTGAG  ACATCAATAA  AACCATGTGT  CAAGTTGACG  CCCCTATGTG  TGGCGATGAA
          6490        6500        6510        6520        6530        6540
     TTGTAATATA  ACTTCAGGGA  CTACCGCGAC  CCCGAGTCCA  CCAAACATTA  CAATAATAGA
          6550        6560        6570        6580        6590        6600
     TGAAAATTCT  ACCTGTATAG  GCGACAACAA  CTGCACAGGA  TTAGGGAAAG  AAGAGGTGGT
          6610        6620        6630        6640        6650        6660
     TGAGTGTGAG  TTCAATATGA  CGGGGCTAGA  ACAAGATAAG  AAAAGGAAGT  ATAATGACGC
          6670        6680        6690        6700        6710        6720
     ATGGTACTCA  AGAGATGTGG  TTTGTGACAA  GACAAACGGA  ACAGGCACAT  GTTACATGAG
          6730        6740        6750        6760        6770        6780
     ACATTGCAAC  ACATCAGTCA  TCAAAGAGTC  ATGTGACAAG  CACTATTGGG  ATGCTATGAA
          6790        6800        6810        6820        6830        6840
     GTTTAGATAC  TGTGCACCAC  CGGGTTTTGC  CCTACTAAGA  TGCAATGATA  CCAACTATTC
          6850        6860        6870        6880        6890        6900
     AGGCTTTGAA  CCTAAGTGCT  CTAAAGTAGT  AGCTGCTTCA  TGCACAAGGA  TGATGGAAAC
          6910        6920        6930        6940        6950        6960
     GCAAACTTCT  ACTTGGTTTG  GCTTTAATGG  CACTAGAGCA  GOAOATAGAA  CATATATCTA
          6970        6980        6990        7000        7010        7020
     TTGGCATGGT  AAOGATAATA  GGACTATCAT  TAGCTTAAAC  AOGTATTATA  ATCTCACAAT
          7030        7040        7050        7060        7070        7080
     GCATTGTAAG  AGACCAGGAA  ATAAGACAGT  TGTACCAATA  ACACTTATGT  CAGGGCGAAG
          7090        7100        7110        7120        7130        7140
     GTTTCACTCT  CGGCCAGTCT  ACAACAAAAA  ACCTGGGCAG  GCATGGTGTT  GGTTTCAAGG
```

FIG. 4F

```
      7150       7160       7170       7180       7190       7200
CAACTGGATA GAAGCCATGC GGGAGGTGAA GCAAACCCTT GCAAAACATC CCAGGTACGG
      7210       7220       7230       7240       7250       7260
AGGAACAAAT GATACAGGAA AAATTAACTT TACGAAGCCA GGAATAGGTT CAGACCCAGA
      7270       7280       7290       7300       7310       7320
AGTGACATAC ATGTGGACTA ACTGCAGAGG AGAATTTCTC TACTGTAATA TGACTTGGTTT
      7330       7340       7350       7360       7370       7380
CCTCAATTGG GTAGAAAATA AGACGAACCA AACACACGGC AACTATGCGC CATGCCATAT
      7390       7400       7410       7420       7430       7440
AAGGCAGATA ATTAACACCT GGCATAAGGT AGGGACAAAT GTATATTTGC CTCCTAGGGA
      7450       7460       7470       7480       7490       7500
AGGGGAGTTG ACCTGCAATT CAACAGTAAC CAGCATAATT GCTAACATTG ACTCAGATGG
      7510       7520       7530       7540       7550       7560
AAATCAGACC AACATTACCT TTAGTGCAGA AGTGGCAGAA CTGTACCGAT TAGAATTGGG
      7570       7580       7590       7600       7610       7620
GGACTACAAA TTGATAGAAG TAACACCAAT TCCGTTCGCA CCTACAAAAG AGAAAAGATA
      7630       7640       7650       7660       7670       7680
TTCCTCGGCT CCAGTGAGGA ACAAAAGAGG TGTGTTCGTG CTAGGGTTCT TGGGTTTTCT
      7690       7700       7710       7720       7730       7740
CGCAGCAGCA GGTTCTGCAA TGGGCGGCNC GTCCTTGACG CTGTCGGCTC AGTCCCGGAC
      7750       7760       7770       7780       7790       7800
TTTACTGGCC GGGATAGTGC AGCAACAGCA ACAGCTGTTG GACGTGGTCA AGAGACAACA
      7810       7820       7830       7840       7850       7860
AGAAATGTTG CGATTGACCG TCTGGGGAAC GAAAAATCTC CAGGCAAGAG TCACTGCTAT
      7870       7880       7890       7900       7910       7920
CGAGAAATAC TTAAAGGACC AGGCACAGCT AAATTCATGG GGATGTGCGT TTAGGCAGGT
      7930       7940       7950       7960       7970       7980
CTGCCACACT ACTGTACCAT GGGTAAATGA CTCCTTAACA CCTGACTGGA ACAATATGAC
      7990       8000       8010       8020       8030       8040
ATGGCAGGAA TGGGAAAAAC GAGTCCACTA CCTAGAGGCA AATATCAGTC AAAGTTTAGA
      8050       8060       8070       8080       8090       8100
ACAGGCACAA ATTCAACAAG AAAAGAATAT GTATGAACTA CAAAAACTAA ATAGCTGGGA
      8110       8120       8130       8140       8150       8160
TGTCTTTGGC AACTGGTTTG ATTTGACCTC CTGGATCAAA TATATTCAAT ATGGAGTTTA
      8170       8180       8190       8200       8210       8220
TATAGTAGTA GGAATAATAG GTTTAAGAAT AGCCATATAT ATAGTGCAAT TGTTAAGTAG
      8230       8240       8250       8260       8270       8280
ACTTAGAAAG GGCTATAGGC CTGTTTTCTC CTCCCCCCCC GGTTATCTCC AACAGATCCA
      8290       8300       8310       8320       8330       8340
TATCCACACG GACAGGGGAC AGCCAGCCAA CGAAGAAACA GAAGAAGACG CCGGAGACGA
```

FIG. 4G

```
      8350       8360       8370       8380       8390       8400
 CAGTGGTTTC GGCTTGTGGC CTTGGCCACT AAACTACATA CAATTCCTGA TCCACCTACT
      8410       8420       8430       8440       8450       8460
 GACTCGCCTC TTGACCGGGC TATACAACAG CTGCAGGGGC TTACTATCCA AGAACTCCCC
      8470       8480       8490       8500       8510       8520
 GACCCGCCGA CTGATCTCCC AGAGTCTAAC AGCAATCAGG GACTGGCTGA GACTTAAGGC
      8530       8540       8550       8560       8570       8580
 GGCCTACCTG CAATATGGGT GCGAGTGGAT CCAAGAAGCG TTCCGAGCAT TCGCAAGGAC
      8590       8600       8610       8620       8630       8640
 TGCGAGAGAG ACTATTGCGG GCGCGTGGAG GGGGTTATGT GAAGCAGCGC AACGCATCGG
      8650       8660       8670       8680       8690       8700
 GAGGGAATC  CTCGCAGTCC CAAGAAGGAT CAGGCAGGGA CCACAAATCC CCCTCCTCTC
      8710       8720       8730       8740       8750       8760
 AGGGACAGCA GTATCAGCAG GGAGAGTTCA TGAACACCCC ATGGAGAACC CCAGCAGCAA
      8770       8780       8790       8800       8810       8820
 TAGGGCAGAA AAATTCATAT AAGCAGCAAA ATATGGATGA TGTAGATTCT GATGATGATG
      8830       8840       8850       8860       8870       8880
 ACCTAGTGGG AGTTCCTGTT ATGCCAAGAG TACCGCTGAG AGAAATGACC TATAAACTGG
      8890       8900       8910       8920       8930       8940
 CAATAGATAT GTCACATTT  ATAAAAGAAA AAGGAGGACT GGAAGGGATA TTTTACAGTA
      8950       8960       8970       8980       8990       9000
 GGGAGAGACA TAGAATCCTA GACTTGTTCC TAGAAAAGGA GGAAGGGATA ATACCAGATT
      9010       9020       9030       9040       9050       9060
 GGCAGAATTA TACTCATGGG CCAGGAACAA GGTACCCAAT GTACTTCGGG TGGCTGTGGA
      9070       9080       9090       9100       9110       9120
 AACTAGTACC AGTAGACATC TCACAAGAGG CAGAGGAAGT AGAGACCAAC TGCTTAGTAC
      9130       9140       9150       9160       9170       9180
 ACCCAGCACA AACAAGCAGA TATGATGACG AGCATGGGGA GACACTAGTT TGGCGGTTTG
      9190       9200       9210       9220       9230       9240
 ACCCCATGCT GGCCTATAGT TACAAGGCCT TCATTCTGCA CCCAGAAGAA TTTGGGCACA
      9250       9260       9270       9280       9290       9300
 AGTCAGGATT GCCAGAGAAA GAGTGGAAGG CAAAACTGAA AGCAAGAGGG ATACCATATA
      9310       9320       9330       9340       9350       9360
 GTGAATAACA GGAACAACCA TACTTGGTCA GGGCAGGAAA TAGCTACTAA GAACAGCTGA
      9370       9380       9390       9400       9410       9420
 GACTGCAGGG ACTTTCCAGA AGGGGCTGTA ACCAAGGGAG GGACATGGGA GGAGCTGGTG
      9430       9440       9450       9460       9470
 GGGAACGCCC TCATATTCTC TGTATAAATG TACCCGCTTC TTGCATTGTA TTC
```

FIG. 5

HIV-D205; corresponding to position 8942-9255 in HIV-2 ROD; homology 71.6%

```
          10         20         30         40         50         60
    TGGAAGGGAT GTATTATAGT GAGAGAAGAC ACAGAATATT AGACACATAT TTTGAGAATG
          70         80         90        100        110        120
    AAGAAGGCAT TGTGTCTGGC TGGCAAAACT ATACTCATGG GCCAGGGATA AGGCATCCCA
         130        140        150        160        170        180
    AATACTTTGG TTGGCTGTGG AAGCTGGTAC CAGTAGAGGT GCCAGCAGCG ACCCGAGAGG
         190        200        210        220        230        240
    AGGAGGAAAC CCATTGCCTA ATGCACCCGG CACAGATCTC CTCATGGGAT GACATCCATG
         250        260        270        280        290        300
    GGGAGACTCT TATCTGGCAG TTTGATTCCC TCCTGGCATA TGATTATGTG GCTTTCAATA
         310
    GGTTTCCAGA AGAGTTT
```

HIV-D205; corresponding to position 718-2510 in HIV-2 ROD; homology 78.6%

```
          10         20         30         40         50         60
    AAAAAATTCT TAAAGTCTTA GCTCCATTAG TACCAACAGG GTCAGAAAAT TTAAAAAGCC
          70         80         90        100        110        120
    TTTTTAATAT CGTCTGCGTC ATTTTTTGCC TGCACGCAGA AGAGAAAGTG AAAGATACAG
         130        140        150        160        170        180
    AGGAAGCAAA AAAGATAGCA CAGAGACATC TAGCGGCGGA CACAGAAAAA ATGCCAGCTA
         190        200        210        220        230        240
    CAAATAAACC AACAGCACCA CCTAGCGGCG GAAATTATCC AGTGCAGCAA CTGGCTGGCA
         250        260        270        280        290        300
    ACTACGTCCA CCTGCCGCTA AGCCCCCGAA CCTTAAATGC TTGGGTAAAG TTAGTAGAAG
         310        320        330        340        350        360
    AAAAGAAGTT CGGGGCAGAA GTAGTACCAG GATTTCAGGC ACTATCAGAA GGATGCACCC
         370        380        390        400        410        420
    CTTATGATAT AAATCAGATG CTAAATTGTG TAGGAGAACA TCAGGCAGCC ATGCAAATTA
         430        440        450        460        470        480
    TTAGAGAAAT AATCAATGAG GAAGCAGCAG ACTGGGACCA GCAACACCCG TCACCAGGCC
```

FIG. 5A

|  490  |  500  |  510  |  520  |  530  |  540  |
|---|---|---|---|---|---|
| CAATGCCGGC | AGGACAACTT | AGGGACCCAA | GAGGGTCAGA | TATAGCAGGA | ACCACCAGCA |
|  550  |  560  |  570  |  580  |  590  |  600  |
| CAGTAGAGGA | ACAGATACAG | TGGATGTACA | GGGCCCAAAA | TCCTGTCCCA | GTGGGAAACA |
|  610  |  620  |  630  |  640  |  650  |  660  |
| TTTATAGAAG | ATGGATTCAA | TTAGGATTGC | AGAAATGTGT | CCGAATGTAC | AATCCTACCA |
|  670  |  680  |  690  |  700  |  710  |  720  |
| ACATATTAGA | CATAAAGCAG | GGACCAAAGG | AGCCCTTCCA | AAGCTATGTA | GATAGATTCT |
|  730  |  740  |  750  |  760  |  770  |  780  |
| ACAAAAGCTT | ACGGGCAGAA | CAAACAGACC | CAGCAGTGAA | AAATTGGATG | ACACAAACAC |
|  790  |  800  |  810  |  820  |  830  |  840  |
| TGCTGATTCA | GAATGCTAAC | CCAGATTGCA | AGTTAGTGCT | TAAGGGCTTG | GGAATGAATC |
|  850  |  860  |  870  |  880  |  890  |  900  |
| CCACCTTAGA | GGAAATGCTA | ACGGCCTGCC | AAGGGATAGG | AGGCCCAGGG | CAGAAGGCAA |
|  910  |  920  |  930  |  940  |  950  |  960  |
| GGCTAATGGC | CGAAGCCTTA | AAGAGGCCC | TAACACCTGC | ACCCATACCG | TTTGCTGCCG |
|  970  |  980  |  990  |  1000  |  1010  |  1020  |
| TTCAACAAAA | AGCAGGGAAG | AGAGGGACAG | TGACATGCTG | GAACTGTGGC | AAACAGGGAC |
|  1030  |  1040  |  1050  |  1060  |  1070  |  1080  |
| ACACAGCCAG | GCAATGCAGG | GCCCCTAGAA | GACAGGGATG | CTGGAAATGT | GGAAAAACAG |
|  1090  |  1100  |  1110  |  1120  |  1130  |  1140  |
| GACACATCAT | GTCAAAATGC | CCAGAAAGAC | AGGCGGGTTT | TTTAGGGTTA | GGACCCTGGG |
|  1150  |  1160  |  1170  |  1180  |  1190  |  1200  |
| GAAAGAAGCC | TCGCAACTTC | CCCATGACCC | AAGTGCCTCA | GGGAGTGACA | CCATCTGCAC |
|  1210  |  1220  |  1230  |  1240  |  1250  |  1260  |
| CCCCGATGAA | CCCAGCAGAG | GGCATGACAC | CTCGGGGGGC | GACACCTCT | GCGCCCCCTG |
|  1270  |  1280  |  1290  |  1300  |  1310  |  1320  |
| CAGATCCAGC | AGTGGAGATG | CTGAAAAGTT | ACATGCAGAT | GGGGAGACAA | CAGAGAGAGA |
|  1330  |  1340  |  1350  |  1360  |  1370  |  1380  |
| GCCGAGAGAG | ACCCTACAAG | GAGGTGACAG | AGGATTTGCT | GCACCTCAAT | TCTCTCTTTG |
|  1390  |  1400  |  1410  |  1420  |  1430  |  1440  |
| GAGAAGACCA | GTAGTCAAAG | CATGTATCGA | GGGTCAGTCA | GTAGAAGTAT | TACTAGACAC |
|  1450  |  1460  |  1470  |  1480  |  1490  |  1500  |
| AGGAGTTGAC | GACTCAATAG | TAGCAGGGAT | AGAATTAGGT | AGCAATTACA | CCCCAAAAAT |
|  1510  |  1520  |  1530  |  1540  |  1550  |  1560  |
| AGTAGGAGGG | ATAGGAGGGT | TCATAAATAC | CAAAGAATAC | AAAGATGTAG | AAATAGAAGT |
|  1570  |  1580  |  1590  |  1600  |  1610  |  1620  |
| AGTGGGAAAA | AGAGTAAGGG | CAACTATAAT | GACAGGAGAT | ACCCCAATAA | ACATTTTTGG |

FIG. 5B

|  1630 |  1640 |  1650 |  1660 |  1670 |  1680 |
|---|---|---|---|---|---|
| CAGAAATATT | TTAAATACCT | TGGGCATGAC | TTTAAATTTC | CCAGTGGCAA | AGGTAGAACC |
|  1690 |  1700 |  1710 |  1720 |  1730 |  1740 |
| AGTAAAAGTT | GAGTTAAAAC | CTGGAAAAGA | TGGGCCAAAG | ATCAGACAAT | GGCCTCTATC |
|  1750 |  1760 |  1770 |  1780 |  1790 | |
| CAGGGAAAAG | ATACTAGCCC | TCAAAGAAAT | CTGTGAAAAA | ATGGAAAAGG | |

HIV-D205; corresponding to position 2877-7293 in HIV-2 ROD; homology 75.1%

|  10 |  20 |  30 |  40 |  50 |  60 |
|---|---|---|---|---|---|
| AGGTATTAGA | TCCTTTTAGA | AAGGCCAACA | GCGATGTCAT | TATAATTCAG | TACATGGATG |
|  70 |  80 |  90 |  100 |  110 |  120 |
| ACATCCTTAT | AGCAAGTGAC | AGAAGTGATC | TGGAGCACGA | CAGGGTAGTG | TCCCAACTAA |
|  130 |  140 |  150 |  160 |  170 |  180 |
| AAGAGTTATT | AAATGACATG | GGATTCTCTA | CCCCAGAAGA | AAAGTTCCAA | AAAGACCCTC |
|  190 |  200 |  210 |  220 |  230 |  240 |
| CGTTCAAATG | GATGGGTTAT | GAGCTCTGGC | CAAAAAAGTG | GAAACTGCAA | AAAATACAAC |
|  250 |  260 |  270 |  280 |  290 |  300 |
| TGCCAGAAAA | AGAAGTTTGG | ACAGTGAATG | CAATTCAAAA | ACTGGTAGGA | GTATTAAACT |
|  310 |  320 |  330 |  340 |  350 |  360 |
| GGGCAGCTCA | ACTCTTTCCT | GGAATTAAGA | CAAGGCACAT | ATGCAAACTA | ATTAGGGGAA |
|  370 |  380 |  390 |  400 |  410 |  420 |
| AGATGACCCT | AACAGAAGAA | GTACAGTGGA | CAGAACTAGC | AGAAGCAGAG | CTACAGGAGA |
|  430 |  440 |  450 |  460 |  470 |  480 |
| ATAAAATCAT | CTTAGAACAG | GAACAAGAAG | GATCCTACTA | CAAGGAAAGG | GTACCGCTAG |
|  490 |  500 |  510 |  520 |  530 |  540 |
| AAGCAACAGT | ACAGAAAAAC | CTAGCAAATC | AGTGGACATA | CAAAATTCAT | CAGGGAAATA |
|  550 |  560 |  570 |  580 |  590 |  600 |
| AAGTCCTAAA | AGTAGGAAAA | TATGCAAAGG | TTAAAAACAC | GCACACCAAC | GGGGTAAGAC |
|  610 |  620 |  630 |  640 |  650 |  660 |
| TACTGGCACA | TGTAGTTCAG | AAAATAGGCA | AAGAAGCCCT | AGTCATCTGG | GGAGAGATAC |
|  670 |  680 |  690 |  700 |  710 |  720 |
| CAGTGTTCCA | TCTGCCAGTA | GAAAGAGAGA | CATGGGACCA | GTGGTGGACA | GATTACTGGC |
|  730 |  740 |  750 |  760 |  770 |  780 |
| AAGTAACCTG | GATCCCAGAG | TGGGACTTTG | TCTCGACCCC | ACCATTAATA | AGACTAGCCT |
|  790 |  800 |  810 |  820 |  830 |  840 |
| ACAACCTAGT | CAAAGACCCC | CTAGAAGGGA | GAGAAACCTA | CTACACAGAT | GGGTCCTGCA |

FIG. 5C

|  850 | 860 | 870 | 880 | 890 | 900 |
|---|---|---|---|---|---|
| ATAGAACCTC | AAAGGAAGGA | AAAGCAGGAT | ATGTCACTGA | CAGGGGAAAA | GATAAGGTTA |
| 910 | 920 | 930 | 940 | 950 | 960 |
| AAGTGTTAGA | ACAGACAACA | AACCAACAAG | CAGAACTTGA | AGCATTTGCA | TTAGCATTAA |
| 970 | 980 | 990 | 1000 | 1010 | 1020 |
| CAGACTCAGA | ACCACAAGTT | AACATCATAG | TAGATTCACA | ATATGTCATG | GGAATAATAG |
| 1030 | 1040 | 1050 | 1060 | 1070 | 1080 |
| CTGCACAGCC | AACAGAAACA | GAATCACCAA | TAGTAGCAAA | AATAATTGAA | GAAATGATCA |
| 1090 | 1100 | 1110 | 1120 | 1130 | 1140 |
| AAAAAGAGGC | AGTATATGTA | GGATGGGTAC | CAGCTCACAA | GGGACTGGGT | GGTAATCAGG |
| 1150 | 1160 | 1170 | 1180 | 1190 | 1200 |
| AAGTAGACCA | CCTAGTAAGT | CAAGGAATCA | GACAGGTCTT | GTTCCTAGAA | AAAATAGAAC |
| 1210 | 1220 | 1230 | 1240 | 1250 | 1260 |
| CAGCCCAGGA | AGAGCATGAA | AAATATCATG | GCAATGTAAA | AGAACTGGTC | CATAAATTCG |
| 1270 | 1280 | 1290 | 1300 | 1310 | 1320 |
| GAATTCCACA | ATTAGTGGCA | AAACAGATAG | TAAATTCCTG | TGATAAATGC | CAACAAAAAG |
| 1330 | 1340 | 1350 | 1360 | 1370 | 1380 |
| GGGAAGCTAT | TCATGGACAG | GTAAATGCAG | ACCTAGGGAC | ATGGCAGATG | GACTGTACAC |
| 1390 | 1400 | 1410 | 1420 | 1430 | 1440 |
| ATTTAGAAGG | AAAAATTATA | ATAGTGGCAG | TCCATGTAGC | CAGTGGGTTT | ATAGAAGCAG |
| 1450 | 1460 | 1470 | 1480 | 1490 | 1500 |
| AGGTAATACC | CCAAGAGACA | GGAAGACAGA | CAGCTCTCTT | CCTACTAAAG | TTGGCCAGCA |
| 1510 | 1520 | 1530 | 1540 | 1550 | 1560 |
| GATGGCCTAT | CACACACCTA | CACACAGACA | ACGGTGCCAA | CTTCACCTCA | CCAAGTGTAA |
| 1570 | 1580 | 1590 | 1600 | 1610 | 1620 |
| AGATGGTAGC | CTGGTGGGTA | GGAATAGAAC | AAACTTTTGG | AGTACCCTAT | AACCCACAAA |
| 1630 | 1640 | 1650 | 1660 | 1670 | 1680 |
| GTCAAGGAGT | AGTGGAAGCA | ATGAACCATC | ACCTGAAAAA | TCAAATAGAC | AGACTCAGAG |
| 1690 | 1700 | 1710 | 1720 | 1730 | 1740 |
| ACCAAGCAGT | ATCAATAGAG | ACAGTTGTAC | TAATGGCAAC | TCACTGCATG | AATTTTAAAA |
| 1750 | 1760 | 1770 | 1780 | 1790 | 1800 |
| GAAGGGGAGG | AATAGGGGAT | ATGACCCCTG | CAGAAAGACT | AGTTAACATG | ATAACCACAG |
| 1810 | 1820 | 1830 | 1840 | 1850 | 1860 |
| AGCAAGAAAT | ACAGTTCTTC | CAAGCAAAAA | ATTTAAAATT | TCAAAATTTC | CAGGTCTATT |
| 1870 | 1880 | 1890 | 1900 | 1910 | 1920 |
| ACAGAGAAGG | CAGAGATCAA | CTCTGGAAGG | GACCTGGTGA | ACTATTGTGG | AAAGGGGAAG |
| 1930 | 1940 | 1950 | 1960 | 1970 | 1980 |
| GAGCAGTCAT | CATAAAGGTA | GGGACAGAAA | TCAAAGTAGT | ACCCAGGAGA | AAAGCAAAAA |

FIG. 5D

```
      1990       2000       2010       2020       2030       2040
  TTATAAGGCA CTATGGAGGA GGAAAAGGAT TGGATTGTAG TGCCGACATG GAGGATACCA
      2050       2060       2070       2080       2090       2100
  GGCAGGCTAG AGAGATGGCA CAGTCTGATT AAGTATCTTA AGTATAGAAC AGGAGAGTTG
      2110       2120       2130       2140       2150       2160
  CAACAGGTCT CTTATGTCCC TCACCACAAG GTAGGATGGG CTTGGTGGAC TTGCAGTAGA
      2170       2180       2190       2200       2210       2220
  ATAATATTTC CCCTAAACAA AGGAGCATGG CTAGAAGTCC AAGGATATTG GAACCTAACC
      2230       2240       2250       2260       2270       2280
  CCAGAAAGGG GATTCTTGAG CTCCTATGCT GTAAGACTAA CATGGTATGA GAGGAACTTT
      2290       2300       2310       2320       2330       2340
  TATACAGATG TAACACCTGA TGTGGCAGAC CAGCTACTGC ATGGGTCTTA TTTCTCTTGC
      2350       2360       2370       2380       2390       2400
  TTTTCAGCCA ATGAAGTAAG GAGAGCCATC AGGGGAGAAA AGATATTGTC CTACTGCAAC
      2410       2420       2430       2440       2450       2460
  TATCCATCAG CTCACGAAGG GCAGGTACCA AGCTTACAGT TTCTAGCCCT AAGGGTCGTA
      2470       2480       2490       2500       2510       2520
  CAGGAAGGAA AAAATGGATC CCAGGGAGAG AGTGCCACCA GGAAACAGCG ACGAAGAAAC
      2530       2540       2550       2560       2570       2580
  AGTAGGAGAA GCATTCGCTT GGCTAGAAAG AACAATAACA GAGCTCAACA GGGTAGCGGT
      2590       2600       2610       2620       2630       2640
  CAACCATTTG CCCCGAGAAC TTATTTTCCA GGTCTGGCAG AGGTCTTGGG CATACTGGCG
      2650       2660       2670       2680       2690       2700
  TGAGGAACAG GGCATGTCAA TTAGCTATAC CAAATATAGA TACTTGTTGC TAATGCAGAA
      2710       2720       2730       2740       2750       2760
  AGCAATGTTT GTGCACTATA CAAAGGGCTG TAGGTGCCTG CAGGAGGGCC ATGGGCCAGG
      2770       2780       2790       2800       2810       2820
  GGGATNGAGA TCAGGACCTC CTCCTCCTCC TCCCCCAGGC CTGGCCTAAT GGCAGAAGCA
      2830       2840       2850       2860       2870       2880
  GCCCCAGAGA TCCCTCCAGA GAACGAGAAC CCACAAAGAG AACCGTGGGA AGAGTGGATA
      2890       2900       2910       2920       2930       2940
  GGGGAGATCC TGGAGGAAAT AAAGCAAGAA GCCTTAAAGC ATTTTGATCC TCGCTTGCTA
      2950       2960       2970       2980       2990       3000
  ACTGCGCTTG GTAACTTTAT CTACAGTAGG CATGGAGATA CCCTTGCAGG AGCAGGAGAG
      3010       3020       3030       3040       3050       3060
  CTCATTAAAA TCCTCCAACG AGCNCTCTTC CTCCACTTCA GAGCCGGTTG TCAACACTCA
      3070       3080       3090       3100       3110       3120
  AGGATTGGAC AATCAGGGGG AGGAAATCCT CTCTCAACTA TACCGCCCCC TTAAGGCATG
```

FIG. 5E

```
      3130       3140       3150       3160       3170       3180
 CGATAATACA TGCTACTGTA AGAAATGCTG CTACCATTGC CAGCTTTGTT TTCTTAAAAA
      3190       3200       3210       3220       3230       3240
 GGGTCTTGGG ATATGTTATG ACCGCTCGAG AAGGAGATCT GCAAAAGAG CTAAGACTAC
      3250       3260       3270       3280       3290       3300
 TGCACCTTCT GCACCAGACA AGTGAGTATG GCATATTTTA GCAGCCGCCT GCCTATTGCG
      3310       3320       3330       3340       3350       3360
 CTCCTGCTTA TAGGTATCAG TGGGTTTGTA TGTAAACAAT ATGTTACTGT CTTCTATGGC
      3370       3380       3390       3400       3410       3420
 ATACCCGCAT GGAGGAACGC AACAGTTCCC CTCATTTGTG CAACCACAAA CAGAGACACC
      3430       3440       3450       3460       3470       3480
 TGGGGAACTG TACAGTGTCT CCCAGACAAT GGTGACTACA CTGAGATCAG GCTAAACATA
      3490       3500       3510       3520       3530       3540
 ACAGAGGCTT TTGATGCATG GGATAATACA GTGACACAAC AGGCAGTAGA TGATGTGTGG
      3550       3560       3570       3580       3590       3600
 AGACTCTTTG AAACCTCCAT AAAACCATGT GTCAAACTAA CCCCACTGTG TGTGGCAATG
      3610       3620       3630       3640       3650       3660
 AACTGTAGTA AAACCGAAAC AAACCCAGGG AATGCCAGTA GTACTACCAC CACTAAGCCT
      3670       3680       3690       3700       3710       3720
 ACTACCACCT CTCGTGGGCT GAAAACGATT AACGAAACAG ACCCATGCAT AAAAAATGAC
      3730       3740       3750       3760       3770       3780
 AGCTGCACAG GACTAGGAGA AGAGGAAATA ATGCAATGTA ATTTTAGTAT GACGGGACTA
      3790       3800       3810       3820       3830       3840
 AGAAGAGATG AGCTAAAACA ATATAAAGAC ACCTGGTACT CAGAAGATTT AGAGTGTAAT
      3850       3860       3870       3880       3890       3900
 AATACCAGGA AGTAATACCA GCAGTGCTAT ATAAGAACCT GCAACACAAC AATTATCCAA
      3910       3920       3930       3940       3950       3960
 GAGTCATGTG ACAAACATTA TTGGGACAGC TTAAGGTTTA GGTATTGTGC TCCCCCGGGG
      3970       3980       3990       4000       4010       4020
 TTTTTTCTAC TAAGATGTAA TGATACCAAC TATTCAGGCT TCATGCCCAA CTGCAGTAAG
      4030       4040       4050       4060       4070       4080
 GTAGTAGCGT CCTCCTGCAC AAGAATGATG GAAACACAGT CCTCTACATG GTTTGGCTTC
      4090       4100       4110       4120       4130       4140
 AATGGTACAA GGGCAGAGAA CAGGACATAT ATATATTGGC ATGAAAAAGA CAATAGGACC
      4150       4160       4170       4180       4190       4200
 ATCATAAGCT TAAATACATA CTATAATTTG TCAATACACT GTAAGAGGCC AGGAAACAAG
      4210       4220       4230       4240       4250       4260
 ACGGTTGTAC CAATAAGAAC CGTGTCAGGA CTACTTTTCC ATTCACAGCC TATCAATAAG
```

FIG. 5F

```
      4270       4280       4290       4300       4310       4320
AGACCCAGAC AAGCTTGGTG CTGGTTTAAG GGAAACTGGA CAGAAGCCAT AAAGGAGGTG
      4330       4340       4350       4360       4370       4380
AAAAGGACCA TCATAAAACA TCCCAGGTAT AAAGGAGGTG CAAAAAATAT CACAAGCGTA
      4390       4400       4410
AAGTTAGTAT CAGAACATGG AAAAGGTTCA GATC
```

FIG. 6

|  | Position | nt ho | AA ho |
|---|---|---|---|
| R | 1-173 | 96.0 | |
| U5 | 174-299 | 94.4 | |
| 5'-untransl. | 300-545 | 93.5 | |
| gag | 546-2114 | 88.1 | 89.1 |
| pol | 1829-4939 | 88.7 | 89.6 |
| vif | 4869-5516 | 88.7 | 82.9 |
| vpx | 5344-5682 | 86.7 | 89.4 |
| vpr | 5682-5999 | 83.0 | 74.5 |
| tat ex 1 | 5845-6140 | 84.5 | 73.5 |
| rev ex 1 | 6071-6140 | 87.1 | 82.6 |
| tat ex 2 | 8307-8403 | 80.4 | 75.0 |
| rev ex 2 | 8307-8539 | 78.5 | 70.0 |
| nef | 8557-9327 | 82.6 | 73.9 |
| U3 | 8942-9496 | 85.4 | |

FIG. 7

| HIV-2_D205.7 gene | position | HIV-2_ROD | HIV-2_NIHZ | HIV-2_D194 | SIV_MAC | SIV_AGM | HIV-1_BRU |
|---|---|---|---|---|---|---|---|
| gag | 720–1826 | 80.5/85.6 | | | | | |
| gag | 1860–2114 | 83.1/77.6 | | | | | |
| pol | 1859–2510 | 80.2/72.5 | | | | | |
| pol | 2877–4948 | 78.3/83.5 | | | | | |
| protease | 2084–2381 | 84.0/81.0 | 83.0/84.8 | 84.8/86.8 | 76.3/83.8 | 57.8/47.1 | 60.4/48.5 |
| vif | 4869–5516 | 72.0/68.5 | 70.9/67.9 | 72.4/66.5 | 71.8/60.6 | 53.8/34.7 | 47.9/33.0 |
| vpx | 5344–5682 | 76.1/74.1 | 73.5/68.1 | 74.6/77.9 | 75.2/77.0 | 50.8/34.7 | |
| vpr | 5682–5999 | 78.8/69.8 | 77.7/69.8 | 74.2/59.4 | 78.9/76.4 | | 51.9/47.3 |
| tatex1 | 5845–6140 | 78.4/66.3 | 79.1/68.4 | 74.7/63.3 | 81.1/66.3 | 33.1/38.1 | 33.6/34.0 |
| revex1 | 6071–6140 | 67.1/61.9 | 68.6/60.9 | 67.1/52.2 | 70.0/60.9 | 45.5/28.6 | 38.2/40.4 |
| nef | 8557–9255 | 72.1/69.5 | | | | | |
| env | 6147–7293 | 70.0/67.0 | | | | | |

FIG. 8

| HIV-2$_{D205.7}$ position | HIV-2$_{ROD}$ | HIV-2$_{NIHZ}$ | HIV-2$_{D194}$ | SIV$_{MAC}$ | SIV$_{AGM}$ | HIV-1$_{BRU}$ |
|---|---|---|---|---|---|---|
| 8942-9255 | 71.6 | 77.0 | 68.8 | 66.4 | 56.3 | 54.7 |
| 718-1825 | 80.5 | 80.8 | 80.3 | 79.1 | 65.1 | 63.8 |
| 1859-2510 | 80.2 | 74.6 | 75.0 | 78.8 | 55.6 | 56.9 |
| 2877-7293 | 75.1 | 74.8 | 75.4 | 74.0 | 58.0 | 54.6 |
| Total | 75.9 | 75.9 | 75.9 | 75.0 | 58.9 | 56.4 |

FIG. 10

|  | HIV-D194<br>(numbers refer<br>to Fig. 4) | HIV-D205<br>(numbers refer<br>to Fig. 5.1–5.3) | HIV-2 ROD<br>(for comparison)<br>(numbers refer to<br>(Guyader et al.)) |
|---|---|---|---|
| gag | 547–2113 | 3–1394(5.2, part.) | 546–2114 |
| pol | 1831–4938 | 1049–1789 (5.2, part.)<br>3–2072 (5.3, part.) | 1829–4939 |
| vif | 4868–5515 | 1993–2643 (5.3) | 4869–5516 |
| vpx | 5343–5681 | 2474–2809 (5.3) | 5344–5682 |
| vpr | 5881–5998 | 2809–3126 (5.3) | 5682–5999 |
| tat exxon 1<br>tat exxon 2 | 5844–6139<br>8276–8372 | 2972–3261 (5.3) | 5845–6140.<br>8307–8403 |
| rev exxon 1<br>rev exxon 2 | 6070–6140<br>8276–8517 | 3198–3261 (5.3, part.) | 6071–6140<br>8307–8539 |
| env | 6146–8701 | 3266–4413 (5.3, part.) | 6147–8720 |
| nef | 8535–9308 | 3–317 (5.1, part.) | 5557–9327 |

FIG. 11 gp 41/40

```
                              ProValArgAsnLysArgGly
5' -GGAATTCCATGGTACCAGTGAGGAACAAAAGAGGT
    CCTTAAGGTACCATGGTCACTCCTTGTTTTCTCCA.....................
    EcoR1, Nco1, Kpn1
```

```
                    Stop.....
..............TCGCCCTCCTGTGATAGTAAGCTTCC-3'
              AGCGGGAGGACACTATCATTCGAAGG
                                     Hind III
``` p24/27

```
                        ProValGlnGlnAla
5' -GGCCATGGTACCCGTGCAACAGGCAG
    CCGGTACCATGGGCACGTTGTCCGTC.................
    Nco1, Kpn1
```

```
                   Stop.....
..............TGGAAAAGACCAGTAGTGATAAGCTTCC-3'
              ACCTTTTCTGGTCATCACTATTCGAAGG
                                       Hind III
```

HIV-2 VIRUS VARIANTS

This is a continuation of application Ser. No. 07/994,081, filed Dec. 16, 1992, which is abandoned upon the filing hereof which in turn is a continuation of application Ser. No. 07/365,568, filed Jun. 14, 1989, abandoned.

The present invention relates to HIV-2 virus variants, namely Virus HIV D194 and HIV D205 that may be cloned from the corresponding virus isolate HIV D194 (which is deposited with the ECACC, PHLS CAMR, Porton Down, Salisbury, wilts under the accession number ECACC V 87122303) or from the infected cell line HUT 194 (also deposited with the ECACC under the accession number ECACC V 87122306) and from the virus isolate HIV D205 (also deposited with the ECACC under the accession number ECACC V 87122304), respectively, and to the RNA or RNA-fragments and derived therefrom DNA and DNA—fragments and/or proteins and the use thereof for diagnostics and therapy.

These variants are also described in "Molecular cloning of two West African human immunodeficiency virus type 2 isolates which replicate well on macrophages: a Gambian isolate from a case of neurologic acquired immunodeficiency syndrome, and a highly divergent Ghanesian isolate" (Kühnel, H., v. Briesen, H., Dietrich, U., Adamski, M., Mix, D., Biesert, L. Kreutz, R., Immelmann, A., Henco, K., Meichsner, Ch., Andreesen, R., Gelderblom, H. & R übsamen-Waigmann, H., 1989, Proc. Natl. Acad. Sci. 86, 4, 2383–2387.

In diagnostics, two criteria are demanded to be met, namely specificity and sensitivity for the antigen to be detected. In the diagnostics of AIDS the demand for specificity can certainly be complied with by using the isolates HTLV-IIIB and LAV-2 (Guyader, M. et al., "Nature" 326, 1987, 662–669) in order to delimit HIV infections from other infections and, thus, to make a rough assignment into the classes of "HIV-2-related infections" or "HIV-1-related infections". However, a problem is constituted by the sensitivity of the diagnosis. In the range of the so-called seroconversion, i.e. the initial occurrence of the antibody in the infected person, a reduction in sensitivity implies an increase in the number of "falsely negative" test results. Accordingly, it is one main goal to shorten the period between an infection and the detectability of this infection as much as possible by improving the test sensitivity.

A decreased cross reactivity, in the practice of the widely employed ELISA diagnostics, is manifested, for example, in a reduced sensitivity. Thus, the use of the described HIV-1 isolate means about an average reduction of the test sensitivity against HIV-2 sera by the factor of 100 to 1000, whereas the isolate HTLV-IIIB enables almost no detection to be accomplished anymore.

A disastrous principle of the diseases caused by HIV resides in the fact that there is not only one type of each of HIV-1 and HIV-2 virus phenotypes and genotypes. What is to be premised is rather a large group of related viruses, possible even populations which by no way are strictly separated from each other but continuously penetrate one another and undergo some evolutionary development to a more and more increasing divergence, while at the same time they begin by recombination events to exchange between each other parts of the genome. Thus, the existing HIV species form a broad continuous population level in which there are no narrowly delimited subpopulations of one virus variant. There is rather to be presumed that a continuum exists which is subject to permanent fluctuations with time.

The classified virus variants HIV-1 and HIV-2 are representatives of the diffusely delimited subpopulations having a relative low degree of relationship, which is manifested by only a partial cross reactivity. On the other hand, there are variants of the HIV-1 group (Rübsa-men-Waigmann, H. et al., "AIDS-Forschung" 10, 1987, 572–575; R übsamen-Waigmann, H. et al., J. Med. Virol. 19, 1986, 335–344; v. Briesen, H. et al., J. Med. Vi-rol. 23, 1987, 51–66), which do significantly stronger cross-react with HIV-2 than the first characterized HIV-1 isolate itself (Hahn, B. et al., "Nature" 312, 1984, 166–169). A commercial product consisting of such an isolate diagnoses distinctly more sera as being HIV-2 positive than does the described standard isolate HTLV-IIIB.

An ideal diagnostic or therapeutic product should contain at least one representative from the populations as significantly biologically distinguished from one another.

HIV-1 viruses in a multitude of highly polymorphic genetic mutants may cause different diseases such as ARC, LAS, AIDS and encephalopathies (ARC: AIDS-related complex, LAS: lymphadenopathy syndrome, AIDS: acquired immune deficiency syndrome). Cloned virus variants are distinguished in sequence and restriction pattern, even if they have been isolated at the same time, at the same place and even from the same patient (Rübsamen, H. et al., 1986). It could be shown that virus variants of the HIV-1 type are distinguished in some virus antigens up to about 15%. HIV-2's are even different in more than 40% of the amino acids in some antigens, substitutions, insertions and deletions having been considered (Guyader, M. et al., 1987; Rabson, A. B. & Martin, M. A. "Cell" 40, 1985, 477–480).

The present invention provides two variants of the HIV-2 virus. One variant was isolated from a clinically asymptomatic patient, and one variant was isolated from a patient suffering from terminal so-called neuro-AIDS. The virus isolates proved to be diagnostic agents, relative to DNA/RNA as well as relative to the virus antigens, for serologically and directly identifying infections by the type HIV-2 in the pre-AIDS and AIDS stages.

The virus isolates according to the invention comprise viruses and proviruses, the characteristics of which are identical to those of the disclosed restriction map and the sequence of the cloned partial regions (FIGS. 2–8). Moreover, the virus isolates comprise variants which are distinguished from the viruses and proviruses described above in that they are different in their nucleotide sequences from the above-described viruses only by up to 5%, and preferably by 2%, particularly preferred by 1%.

The virus variants according to the invention may cause lymphadenopathies (further designated as LAS/AIDS) or serious neurological disorders (encephalopathies). Claimed according to the invention are also expression products of said virus variants, and more particularly antigens, preferably in accumulated or pure form, and processes for producing said expression products in full or in parts or in combinations of the parts. The expression products are intended to include all polypeptides in glycosylated and or meristylated forms which have been coded on the positive or negative strand of the cloned RNA or DNA.

A further preferred embodiment consists of cloned DNA sequences capable of hybridizing with genomic RNA and DNA of the virus variants. Claimed according to the invention are stable gen probes containing such DNA sequences which are suitable for the detection of hybridization of those and other HIV variants or related viruses or DNA proviruses in samples to be investigated, more particularly biological or semi-synthetic samples.

A further preferred embodiment of the invention is comprised by virus variants the RNA/DNA of which or respective fragments will hybridize to the virus variants according to the invention under stringent conditions, more particularly c-DNA, genomic DNA, recombinant DNA, synthetic DNA or fragments thereof. These are understood to include variants or fragments which exhibit deletions and insertions in comparison to the virus variants according to the invention.

Stringent conditions of hybridization and washing are meant to be understood as those conditions which ensue in way of experiment or calculation if the melting point of the 100% homologous nucleic acid complexes in conditions of hybridization and washing will be fallen below by not more than 5° C., under the buffer conditions employed.

Also claimed according to the invention are cloned synthetic gen probes which may be derived from the above-described virus variants and can be augmented in vector systems in eukaryotes or prokaryotes. The described cloned DNA fragments are suitable for hybridization with complementary nucleic acids (DNA/RNA) for the purpose of diagnostic detection of the virus variants. The diagnostic tests according to the invention are carried out by using DNA or RNA probes. The probes are radioactive or have been labelled with fluorescent bio- or chemiluminescent groups or enzymes or are specifically detectable with enzymes via coupled reaction systems. The hybridizations may be effected in a homogeneous phase of a solution or in a heterogeneous phase with solid-immobilized nucleic acids, while the solid may be a membrane, particle, cell or tissue, so that the hybridization may also be effected in situ.

From the virus isolates claimed according to the invention, the corresponding DNA sequences (FIG. 2) may be cloned in E. coli bacteria by establishing a genomic lambda-gen bank, starting from the DNA of the lymphocytes infected with the virus isolate. The desired clones are obtained by carrying out a plaque-screening with STLV-III sequences of the gag-pol range. In a more specific way, there may be used as a probe a DNA derived from the published sequence HIV-2 ROD (Guyader, M. et. al., "Nature" 326, 1987, 662–669), or a DNA probe derived from the partial sequences of the isolates HIV-2 D194 and HIV-2 D205 according to the invention. Thus, from FIG. 3 a probe may be derived which under stringent conditions will hybridize only with variants of the type HIV-2 D194, however not with variants of the type HIV-2 ROD.

The diagnostic method based on the use of the viruses claimed according to the invention comprises the following steps: Extraction of RNA or DNA from biological samples, possibly enzymatic processing by restriction enzymes, separation by gel electrophoresis and/or direct blot methods for nucleic acid-binding carriers, and subsequent hybridization with parts of the cloned fragments of the claimed viruses. Hybridizations may also be directly carried out in chemically treated cells or tissues. Therein the origin of the tissues or liquids is insignificant.

Specifically, a process for the in vitro detection of antibodies against expression products of the viruses of the present invention is characterized in that the expression products or parts thereof of the viruses are detected by means of immunological methods. The process is characterized in that the expression products are proteins, peptides or parts thereof which have been coded within the meaning of an open reading frame on the DNA of the proviral partial sequences as characterized in FIG. 9 and are prepared by synthetic or biosynthetic processes.

The process is further characterized in that previously a definite amount or a combination of expression products or parts thereof are fixed on microtiter plates, whereupon subsequently biological samples, diluted or undiluted, are contacted with the coated microtiter plates and after incubation and sequential washing steps can be identified by means of a detecting reagent or of labelled anti-HIV antibodies.

Alternatively, filter strips and plastic strips or rods are used instead of microtiter plates, wherein the expression products of the viruses have been fixed at respective specific positions by isolated application of the different antigens.

The expression products or parts thereof can also be separated by gel electrophoresis and then transferred by blotting whereupon incubation with anti-HIV antibodies and the detection thereof are effected. Detection is effected on solid phase carriers to which the antigen determinants have been bonded, with the solid phase carrier consisting of particles.

Expression products can be virus antigens derived from in vitro-infected cells, said antigens being contacted with biological test materials as antigens bonded to fixed cells, and that the subsequent antibody bonding can be determined with immunological detection reagents by means of an apparatus, for example with a cytofluorimeter, or visually.

The antigens can be determined by competitive ELISA. HIV-related nucleic acids (DNA and RNA) can be detected in biological samples, cells and in isolated form by using the nucleic acids according to the present invention.

Expression products can be supplemented by materials which are related to other HIV variants, which, however, are distinguished in their biological properties from the materials of the isolates of the present invention.

For diagnostic and therapeutic goals the described DNA segments may also be employed for expressing coded antigens, parts thereof or combinations thereof with alien antigens. Therein the DNA segments under aimed control of regulation sequences are introduced into pro- or eukaryotic target cells, tissues or multiple-cell organisms to stimulate these to produce the accordingly coded antigens, parts thereof or combinations thereof with alien antigens. Antigens can be detected via the reaction with Anti-HIV-2 antibodies, more particularly from the sera of the respective patients. Antigens having longer open reading frames (>50 amino acids) lend themselves as well those which are subject to splicing processes on the RNA level and are only thus composed to form the longer open reading frames.

According to the invention further claimed are polypeptides originating from the cloned virus variants according to the invention to detect such antigens in the material under investigation which contain similar antigen determinants and thereby do immunologically cross-react. This is particularly suitable for the diagnosis of AIDS and pre-AIDS of virus carriers or asymptomatic virus carriers or virus products, respectively, which are derived from blood. Also the serological detection of the antibodies directed against these antigenic polypeptides as expression products of the viruses claimed according to the invention becomes possible by employing conventional systems such as ELISA. The immunogenic polypeptides may be used as protective polypeptides as vaccines to cause protection against AIDS infections.

The polypeptides according to the invention are understood to include fragments which are intentionally obtained by means of gen-technological methods, starting from longer open reading frames as well as those obtained by proteolytic enzymes in the production bacterial strains or in vitro by the use of proteases.

The virus isolates according to the invention and the products derived therefrom may be combined with other isolates of the partial population HIV-2 in test systems, that is with those which are as far remote as possible in the described population level such as for example, the isolate HIV-2 ROD (Guyader, M. et al., 1987). Thereby it becomes possible sensitively to detect also populations of remote relationship in one test.

The virus variants according to the invention are highly different from the spectrum of the HIV-1 variants and have a closer molecular relationship to the HIV-2 virus described by Guyader, although they are distinguished therefrom to a significant extent (FIG. 1, FIG. 2, FIG. 3). Also the biological properties are clearly distinguished from the described HIV-2 isolate. Thus, the variants according to the invention, for the effective in vitro re-plication, prefer cells which are derived from myeloidic lines. On the contrary, the virus poorly reproduces itself on lymphocytic lines. This quality especially refers to HIV-D194.

The virus HIV D194 according to the invention exclusively caused encephalopathic symptoms in the infected patient, due to which the patient also deceased after an extremely short time and after a fulminant progress of the disease. Samples of the viruses claimed according to the invention have been deposited in the forms of their isolates at the European Collection of Animal Cell Cultures under the designations HIV D194 (Accession No. V 87122303) and HIV D205 (V 87122304), respectively, according to the Budapest Treaty.

A cell line infected with the virus isolate HIV D194 has been deposited under the designation HUT 194 (ECACC V 87122306) at the above-identified Deposit.

FIG. 1 shows the deviation of the proteins p24 and gp41 from lambda D194 and HIV-2 ROD 27/35 in its nucleotide sequence and amino acid sequence. (Guyader, M. et al., 1987, Nature 326, 662–669.)

FIG. 3 shows a comparative section of a sequence between HIV-2 ROD (Guyader, M. et al., 1987) and HIV-2 D194, which demonstrates the significant divergence of the variant HIV-2 D194 according to the invention in a coding range of the envelope protein gp120.

The section of the sequence shows a range of the gp120 region in comparison to the nucleotide sequence and the corresponding amino acid sequence in the single letter notation between HIV-2 D194 and HIV-2 ROD (Guyader, M. et al., 1987). The indication of the position refers to HIV-2 ROD. (−) symbolizes deletions/insertions. (.) symbolizes identical nucleotides.

FIGS. 4–4G shows a nucleotide sequence, characterizing the clone HIV-D194. Nucleotide positions designated as N or O could not be unambiguously derived from the gel pattern. The sequence starts with R/U5 region the LTR and ends with U5 region.

The sequence shown is derived from subclone L10 (see restriction map). This clone differs from others derived from the same patient/blood sample by around 1% in the nucleotide sequence as it was determined by comparison with 5 kb homologous sequences derived from clone HIV-194.5.

Figure 2:
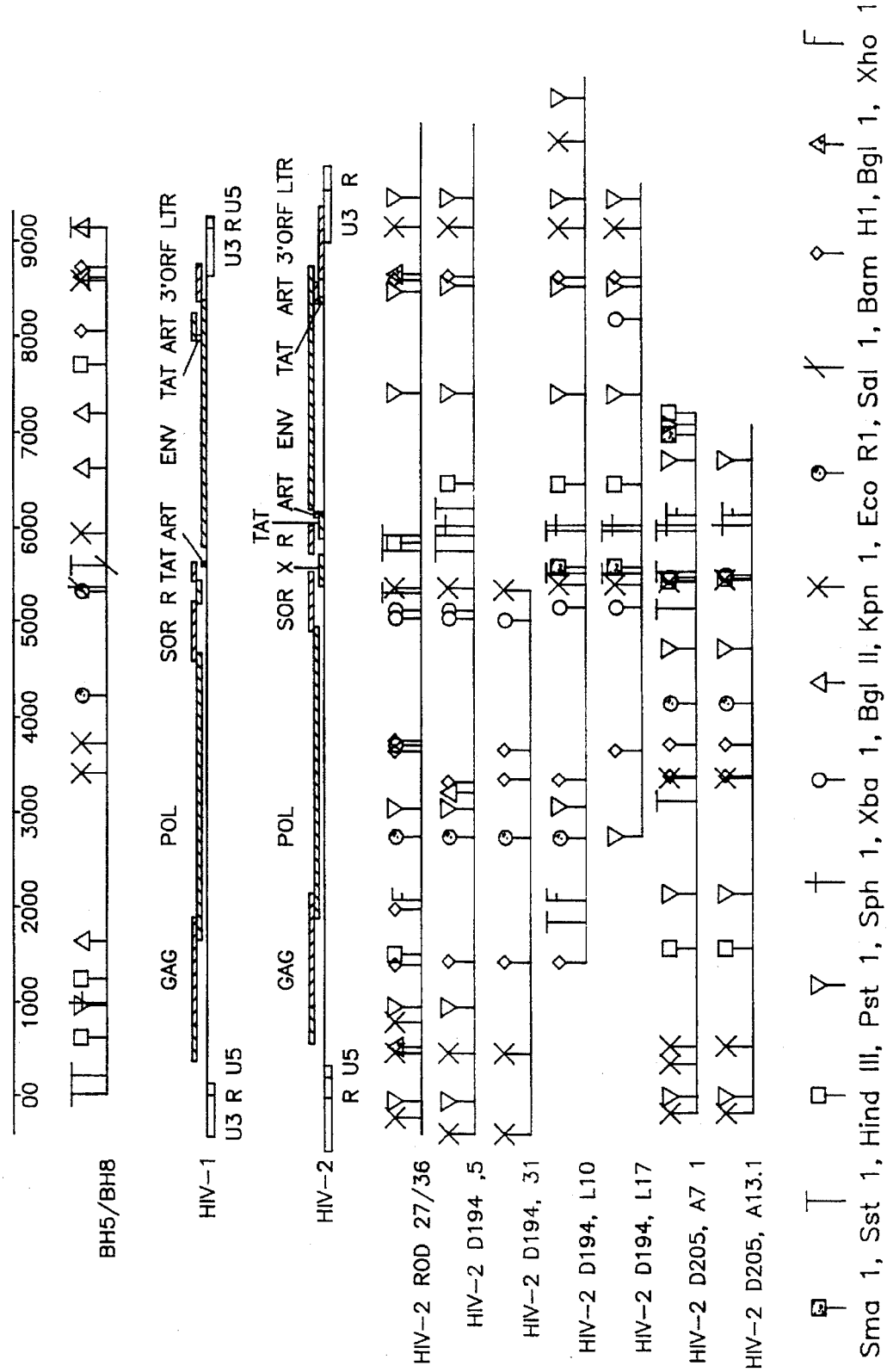
FIG. 2 shows the restriction maps of the virus isolates according to the invention in comparison to known HIV sequences.

FIGS. 5–5F shows the partial nucleotide sequences of HIV-D205 (corresponding to clone HIV-2 A7.1 of FIG. 2).

FIG. 6 shows the sequence homology between HIV-D194 and HIV-2 ROD in (%), separately for the functional elements. The env region is not included because of the very much unrelated internal region shown in FIG. 3. (nt ho=nucleotide homology, AA ho=amino acid homology)

FIG. 7 shows the sequence homology of HIV-2 D205,7 compared to the HIV/SIV group (gene level; nt/aa).

FIG. 8 shows a nucleotide sequence comparison of HIV-2 D205 with HIV and SIV strains (in % homology).

Figure 9:
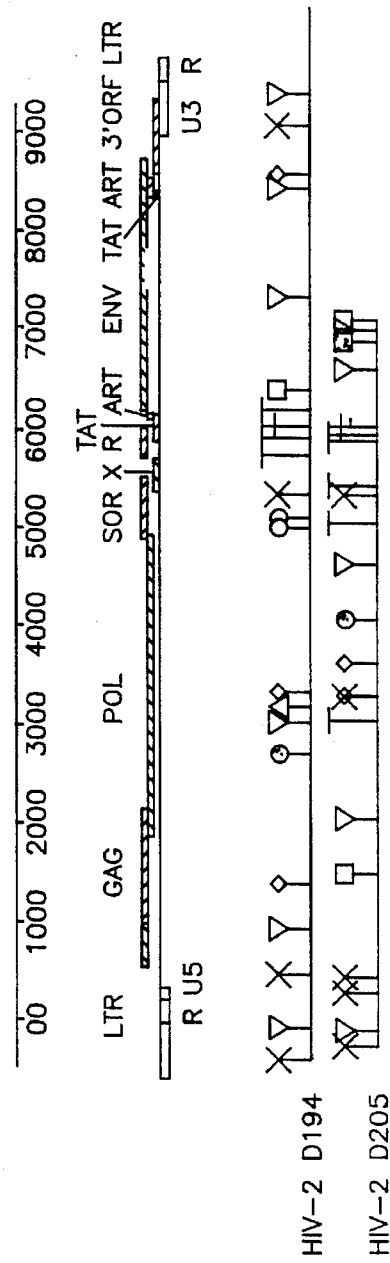

FIG. 9 shows the restriction maps of the proviral partial sequences of the isolates according to the invention.

FIG. 10 shows the correspondence of the open reading frames with functionally known antiviral antigens.

FIG. 11 shows the primer mediated constructions which are inserted as corresponding restriction fragments into the appropriate vectors.

Experimental results and characteristics of HIV-D194 and HIV-D205 are described in Kühnel, H. et al. (1989) Proc. Natl. Acad. Sci. 86, 4, 2383–2387.

The sequence of HIV-D194 shows a lot of so-called "open reading frames" as the fragments of HIV-D205 do. Most of these reading frames can be related to in vivo expressed proteins/antigens by comparison of homologies to previously described HIV-viruses, by comparison of Western blots performed with HIV-D194 and HIV-D205 antigens derived from infected HUT78 or U937 cells and by probing with sera from the corresponding patients and reference sera. FIG. 10 shows the correspondence of the open reading frames (numbers refer to FIG. 4 and 5) with functionally known antiviral antigens.

Other open reading frames are not identified on the level of their expressed antigens defined by function or antibody staining on Western Blot. However, they can be expressed under some circumstances in vivo. Other reading frames, even short ones, can be expressed as well in a way difficult to predict solely on the basis of nucleic acid sequencing data because of splicing processes.

Antigenic determinants on expressed proteins as they are important for the biological function, for target antigens in diagnostics or for immunization are spread all over the expressed linear protein sequence. Parts of these sequences can have more general antigenic properties than others as can be shown by peptide screening/mapping for antigenic sites. These sites can be expressed as single epitopes or as continuous polypeptide or in a version of in vitro or synthetically spliced antigens. Antigenicity of the expressed products can be demonstrated by antigen fixation and blotting in the Western Blot assay. Constructions for antigen expression in *E. coli* can be done by using conventional techniques using synthetic genes, restriction fragments from cloned viral genome segments, trimming products thereof by using exonuclease or DNase I or by using sequence specific synthetic primers (FIG. 11) defining the desired 5' and 3' end of the fragment to be expressed together with appropriate restriction sites. These restriction sites can easily be used for ligation into a panel of expression vectors of different organisms like those derived from PLc24 (Remault et al. 1981 Gene 15, 81–83) with multicloning sites (pEX).

The expressed antigens were shown to specifically react with patients' sera. The p27(24) from gag of HIV-D205 react very sensitively with both typical HIV-1 sera and typical HIV-2 sera (see Kühnel et al). The antigenic sequence corresponding to the region shown in FIG. 3 is highly specific for this particular subfamily of HIV-variants.

EXAMPLE 1

Cloned subfragments such as the Kpn—Kpn fragment comprising the gag-pol region of HIV-D194 are used as probes for HIV-2 type and SIV type sequences by hybridizing under conditions 30°–40° C. less in hybridization and washing conditions appropriate for homologous sequences.

The hybridization of homogenous DNA double helices is usually performed at temperatures of 20°–25° C. below Tm. Tm as the corresponding melting temperature is calculated in an approximation as Tm=81.5°C.+16.6 log M+0.41 (% G+C)–500/n×0.61 (% formamide((see J. Meinkoth & G. Wahl, Anal. Biochem. 138 (1984) 267–284; Boiton, E. T. & McCarthy, B. J., Proc. Natl. Acad. Sci., USA 488 (1962) 1390–1397). Stringent washing conditions for homogenous DNA-double helices are chosen around 5° C. below the Tm calculated as above.

HIV-1 sequences do not show up in blot and in situ hybridization unambiguously, although this region contains the p24/27 coding region which heavily cross-reacts with anti HIV-1 sera. A nucleic acid probe such as shown in and corresponding to FIG. 3, however, highly specifically detects the specific subfamily of HIV-D194 compared to all other known HIV isolates. This is shown by in situ hybridization using run-off RNA of this particular region.

I claim:

1. Virus isolate HIV D194 (ECACC V 87122303) or a virus isolate HIV D205 (ECACC V 87122304).

2. A protein expressed by the virus isolate of claim 1, which is encoded by DNA of the virus isolate.

3. A protien according to claim 2, that is encoded as an open reading frame product.

4. A process for the in vitro detection of antibodies produced against antigens in a biological sample, comprising contacting the protein of claim 2 with a biological sample, and detecting the presence or absence of HIV antibodies bound to the protein.

5. The process of claim 4, wherein the protein is encoded as an open reading frame product.

6. A process for the in vitro detection of antibodies produced against antigens in a biological sample, comprising fixing a plurality of proteins of claim 2 onto a carrier selected form the group consisting of microtiter plates, filter strips, plastic strips, rods, and solid particles;

contacting the carrier with a biological sample;

washing the carrier at least once; and detecting the presence or absence of carrier-fixed protein/HIV antibody complexes.

7. The process according to claim 6, wherein the plurality of protein are antigens of the virus isolate, wherein the carrier is selected form the group consisting of filter strips, plastic strips, rods, and solid particles, and wherein each antigen is fixed at a specific position on the carrier.

8. The process according to claim 7 further comprising separating the antigens by gel electrophoresis prior to fixation, and transferring the separated antigens by blotting.

9. The process according to claim 8, wherein the carrier is solid particles.

10. The process according to claim 4, wherein the protein is present in isolated infected cells bearing antigens.

11. The process of claim 10, further comprising detecting the presence or absence of protein/HIV antibody complexes by adding a detection reagent.

12. The process of claim 11, further comprising determining the level of detection reagent bound to the protein/HIV antibody complexes with a cytofluorimeter.

13. The process of claim 11, further comprising determining the level of detection reagent bound to the protein/HIV antibody complexes visually.

14. The process according to claim 10 further comprising detecting the presence or absence of protein/HIV antibody complexes by adding an enzyme-labeled anti-HIV antibody capable of binding to the amino acid/HIV antibody complexes and measuring the activity of the immobilized enzyme label with its corresponding substrate.

* * * * *

UNITED STATES PATENT AND TRADEMARK OFFICE
CERTIFICATE OF CORRECTION

PATENT NO. : 5,637,455
DATED : June 10, 1997
INVENTOR(S) : Karsten HENCO, Hagen von BRIESEN, Andreas IMMELMANN, Herbert KÜHNEL, Ursula DIETRICH, Helga RÜBSAMEN-WAIGMANN, and Michalina ADAMSKI It is certified that error appears in the above-indentified patent and that said Letters Patent is hereby corrected as shown below:

TITLE PAGE:

In item [30], Foreign Application Priority Data, change "June 18, 1988" to --June 14, 1988--.

Signed and Sealed this

Twenty-eighth Day of October, 1997

*Attest:*

BRUCE LEHMAN

*Attesting Officer*   *Commissioner of Patents and Trademarks*